United States Patent [19]

Hajos et al.

[11] 4,316,022
[45] Feb. 16, 1982

[54] BENZO-AS-TRIAZINE DERIVATIVES

[75] Inventors: György Hajos; Andras Messmer; Pal Benko; Lujza Petocz; Peter Görog; Ibolya Kasoczky, all of Budapest, Hungary

[73] Assignee: EGYT Gyogyszervegyeszeti Gyar, Budapest, Hungary

[21] Appl. No.: 135,143

[22] Filed: Mar. 28, 1980

[30] Foreign Application Priority Data

Apr. 11, 1979 [HU] Hungary .................... EE 2646

[51] Int. Cl.³ ............... C07D 487/04; C07D 487/14; C07D 401/14; C07D 403/14
[52] U.S. Cl. .................................. 544/184; 544/112
[58] Field of Search ............. 424/249, 248.4, 248.51, 424/248.55, 248.57; 544/184, 112

[56] References Cited

U.S. PATENT DOCUMENTS 3,933,816  1/1976  Szmuszkovicz ............ 544/184
4,017,492  4/1977  Moffett ..................... 544/184

Primary Examiner—John M. Ford
Attorney, Agent, or Firm—Young & Thompson

[57] ABSTRACT

The invention relates to new benzo-as-triazine derivatives of the formulae (I) and (Ia) and pharmaceutically acceptable acid addition salts thereof,

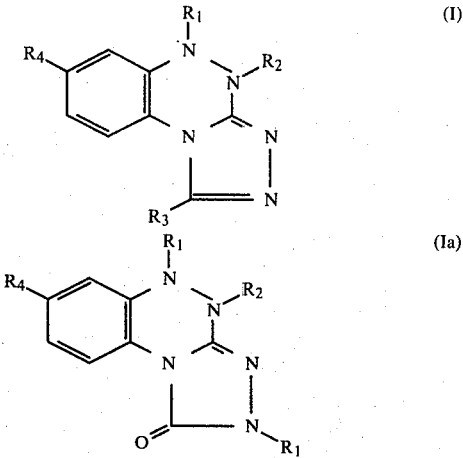

wherein
$R_1$ and $R_2$ each represent hydrogen, a $C_{1-20}$ alkylcarbonyl group, a phenylcarbonyl or phenyl-($C_{1-4}$ alkyl)-carbonyl group having optionally one or more halogen, hydroxy or $C_{1-3}$ alkoxy substituents which may be the same or different, furthermore a pyridylcarbonyl, a pyrazinylcarbonyl, a furylcarbonyl, a chloroacetyl or a $C_{1-4}$ alkoxycarbonyl group, or $R_1$ and $R_2$ may form, together with the adjacent nitrogen atoms, a pyrazole ring having optionally a $C_{1-6}$ alkyl substituent in position 4, with the proviso that one of $R_1$ and $R_2$ is always different from hydrogen, $R_3$ stands for hydrogen, mercapto group, a $C_{1-4}$ alkylmercapto group, amino group, a $C_{1-4}$ alkylamino group, a piperazino group having optionally an N-alkyl or 2-pyridyl substituent, a morpholino group or a piperidino group, and $R_4$ stands for hydrogen, halogen, $C_{1-4}$ alkyl or $C_{1-4}$ alkoxy group.

The compounds of the formulae (I) and (Ia) are prepared by acylating the respective 2,4,5-unsubstituted 4,5-dihydro-benzo-as-triazine derivatives.

The new compounds of the formulae (I) and (Ia) possess analgesic, antiphlogistic and narcosis-potentiating effects.

3 Claims, No Drawings

BENZO-AS-TRIAZINE DERIVATIVES

The invention relates to new benzo-as-triazine derivatives.

The new compounds according to the invention correspond to the formulae (I) and (Ia),

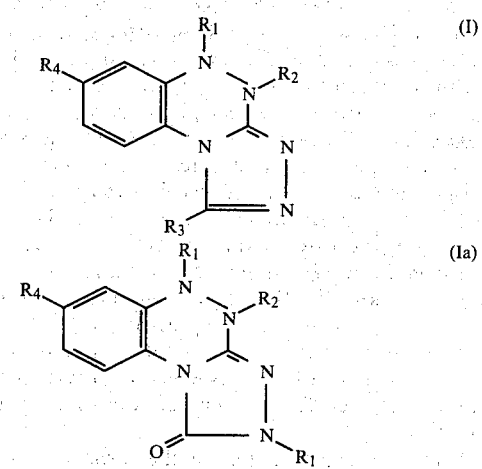

wherein $R_1$ and $R_2$ each represent hydrogen, a $C_{1-20}$ alkylcarbonyl group, a phenylcarbonyl or phenyl-($C_{1-4}$ alkyl)-carbonyl group having optionally one or more halogen, hydroxy or $C_{1-3}$ alkoxy substituents which may be the same or different, furthermore a pyridylcarbonyl, a pyrazinylcarbonyl, a furylcarbonyl, a chloroacetyl or a $C_{1-4}$ alkoxycarbonyl group, or $R_1$ and $R_2$ may form, together with the adjacent nitrogen atoms, a pyrazole ring having optionally a $C_{1-6}$ alkyl substituent in position 4, with the proviso that one of $R_1$ and $R_2$ is always different from hydrogen, $R_3$ stands for hydrogen, mercapto group, a $C_{1-4}$ alkylmercapto group, amino group, a $C_{1-4}$ alkylamino group, a piperazino group having optionally an N-alkyl- or 2-pyridyl substituent, a morpholino group or a piperidino group, and $R_4$ stands for hydrogen, halogen, $C_{1-4}$ alkyl or $C_{1-4}$ alkoxy group.

The scope of the invention also embraces the acid addition salts of the above compounds. Of the salts the pharmaceutically acceptable acid addition salts are particularly preferred.

The term "alkyl" refers to straight-chained or branched saturated aliphatic hydrocarbyl groups, such as methyl, ethyl, n-propyl, isopropyl, n-butyl etc. The term "alkoxy" refers to groups derived from the alkyl groups mentioned above, such as methoxy, ethoxy, n-propoxy etc. As preferred representatives of the $C_{1-20}$ alkylcarbonyl groups e.g. the acetyl, propionyl and stearoyl groups are to be mentioned. An example of the phenyl-($C_{1-4}$ alkyl)-carbonyl groups is the phenylacetyl group, whereas of the $C_{1-4}$ alkoxycarbonyl groups e.g. the methoxycarbonyl and ethoxycarbonyl groups are to be mentioned.

Preferred representatives of the new compounds having the formulae (I) and (Ia) are those wherein $R_1$ and $R_2$ each represent hydrogen, acetyl, propionyl, stearoyl, benzoyl, phenylacetyl, chloroacetyl, nicotinoyl or cinnamoyl, or $R_1$ and $R_2$ form together with the adjacent nitrogen atoms a 1,3-dioxo-2-n-butyl-pyrazole or 1,3-dioxo-2-n-propyl-pyrazole group, with the proviso that at least one of $R_1$ and $R_2$ is other than hydrogen, and $R_3$ and $R_4$ are as defined above, and the pharmaceutically acceptable acid addition salts of these compounds.

Of the new compounds having the general formulae (I) and (Ia) the following are particularly preferred:

4,5-diacetyl-4,5-dihydro-s-triazolo[3,4-c]benzo-as-triazine, 4,5-dipropionyl-4,5-dihydro-s-triazolo[3,4-c]benzo-as-triazine, 5-propionyl-4,5-dihydro-s-triazolo[3,4-c]benzo-as-triazine, 1-methylthio-4,5-dipropionyl-4,5-dihydro-s-triazolo[3,4-c]-benzo-as-triazine, 2,4,5-tripropionyl-4,5-dihydro-s-triazolo[3,4-c]benzo-as-triazine-1(2H)-one, 2-n-butyl-1-oxo-3-hydroxy-pyrazolo[1,2-a]-s-triazolo[3,4-c]benzo-as-triazine, 2-n-propyl-1-oxo-3-hydroxy-pyrazolo[1,2-a]-s-triazolo[3,4-c]benzo-as-triazine, and the pharmaceutically acceptable acid addition salts, particularly hydrochlorides, thereof.

The new compounds of the general formulae (I) and (Ia) and their pharmaceutically acceptable acid addition salts are prepared according so that a compound of the general formula (II) or (IIa),

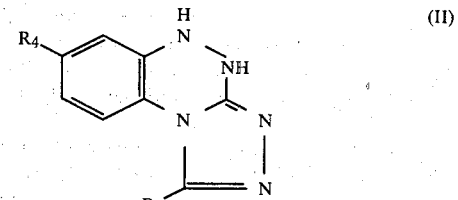

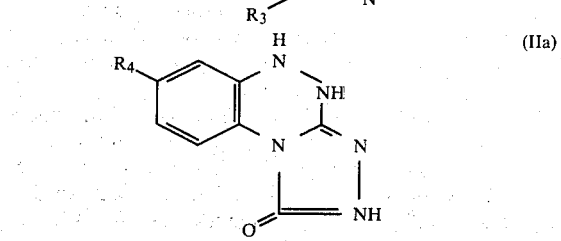

wherein $R_3$ and $R_4$ are as defined above, is reacted with a monofunctional acylating agent of the formula (III),

wherein $R_1$ is as defined above and X stands for a leaving group, or with a bifunctional acylating agent of the formula (IV),

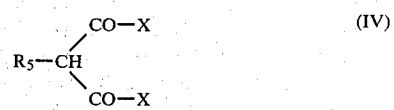

wherein $R_5$ is a $C_{1-6}$ alkyl group or hydrogen and X stands for a leaving group, and, if desired, a resulting triacyl derivative is converted into the respective mono- or diacyl derivative by partial hydrolysis, or, if desired, a resulting diacyl derivative is converted into the respective monoacyl compound by partial hydrolysis, and, if desired, a free base of the formula (I) or (Ia) is converted into its pharmaceutically acceptable acid addition salt, or the free base of the formula (I) or (Ia) is liberated from its salt.

All acylating agents derived from the appropriate aliphatic, aromatic or heterocyclic carboxylic acids (i.e. the free acids themselves or their halides, anhydrides, esters, etc.) capable of acylating a secondary amine can be applied in the process according to the invention.

In most instances the acylating agents can also be applied as reaction medium. In these cases the acylating agent is introduced in excess, and the excess of the acylating agent is removed from the reaction mixture when the reaction terminates. The reaction can also be performed, however, in the presence of an inert organic solvent; in this case no excess of the acylating agent is required.

If a monofunctional acylating agent of the formula (III) is applied in the reaction, mono- or diacyl compounds are obtained, depending on the amount of the acylating agent introduced. If the starting substance and the acylating agent are applied in equimolar amounts, monoacyl compounds of the formula (I), i.e. compounds in which one of $R_1$ and $R_2$ is acyl and the other is hydrogen, are formed, whereas if the acylating agent is applied in excess, the respective diacyl derivatives of the formula (I), wherein both $R_1$ and $R_2$ are acyl groups, are obtained.

The monoacyl derivatives have generally sufficient basicity to form addition salts with acids. Such acid addition salts can be obtained either directly during the acylating reaction, or the isolated monoacyl compounds can be converted into their acid addition salts in a separate step. The diacyl compounds generally do not form acid addition salts.

The pharmaceutically acceptable acid addition salts of the compounds having the formula (I) can be formed with mineral acids (such as hydrochloric, hydrobromic, sulfuric, nitric, phosphoric, etc. acids) or organic acids (such as lactic, maleic, fumaric, tartaric, succinic, etc. acids).

The triacyl compounds of the formula (Ia), in which $R_1$ and $R_2$ both are different from hydrogen, can be prepared by reacting a dihydro-benzo-as-triazine-1(2H)-one of the formula (IIa), wherein $R_4$ stands for hydrogen or halogen, with a monofunctional acylating agent of the formula (III). In such instances the compounds of the formula (IIa), present generally as the keto tautomer, are also acylated on the nitrogen atom in position 2. The resulting 2,4,5-triacyl derivatives of the formula (Ia) do not form acid addition salts.

As bifunctional acylating agents of the formula (IV) preferably the respective malonic acid dihalides (X=halo) or malic acid esters (X=alkoxy) are applied. This reaction provides compounds of the formula (I) in which $R_1$ and $R_2$ form, together with the adjacent nitrogen atoms, a pyrazole-3,5-dione ring with an alkyl substituent in position 4. This alkyl group corresponds to the $R_5$ group of the acylating agent having the formula (IV). The resulting compounds of the formula (I) contain the new pyrazolo[1,2-a]-s-triazolo[3,4-c]benzo-as-triazine ring system and they are formed in a single step. If a malonic acid halide is applied as acylating agent, the reaction is performed preferably in the presence of an acid binding agent, such as triethylamine, dimethylamine, etc. It is preferred to apply the acid binding agent in a quantity not exceeding 75% of the equimolar amount, because in this case the product is obtained under a shorter reaction time in a more easily separable form.

The dihydro derivatives of the formula (II) are reacted with the malic acid esters of the formula (IV) preferably under the conditions conventionally applied in the preparation of acid amides.

As follows from their chemical structures, the new pyrazole-3,5-dione derivatives may also appear in the form of the respective enols. Accordingly, the reaction yields 1-oxo-3-ol, 1-ol-3-oxo or 1,3-diol tautomers or various mixtures thereof. For the sake of clarity these compounds are termed throughout the specification and claims as 1-oxo-3-ol derivatives, formed generally as major components; nevertheless this term covers all of the possible isomers and isomeric mixtures.

The diacyl derivatives of the formula (I), in which $R_1$ and $R_2$ both stand for an acyl group each can be converted into the respective monoacyl compounds by partial hydrolysis. Hydrolysis can be performed in an alkaline medium, e.g. in the presence of an alkali metal hydroxide (such as sodium or potassium hydroxide) or an alkali metal carbonate (such as sodium or potassium carbonate). The reaction proceeds even at room temperature.

The triacyl compounds of the formula (Ia) can be converted into the respective mono- or diacyl derivatives by partial hydrolysis. This reaction can be performed by methods generally known in the organic chemistry.

Most of the compounds having the formula (II), applied as starting substances in the process of the invention, are new. 4,5-Dihydro-s-triazolo[3,4-c]benzo-as-triazine can be prepared from s-triazolo[3,4-c]benzo-as-triazine by reduction, which can be performed in a manner known per se, e.g. by catalytic hydrogenation or by utilizing chemical reducing agents, such as sodium dithionite (Sasaki and Murata: Chem. Ber. 1969, 3818). The starting substances of the formula (II) bearing a substituent on the benzene ring can be prepared by the above method from the appropriately substituted phenylhydrazine derivatives. The starting substances of the formula (II) bearing a substituent in position 1 can be prepared by halogenating the respective 1-unsubstituted compound of the general formula (II), utilizing preferably bromine as halogenating agent, and reacting the resulting 1-halo (preferably 1-bromo) derivative with the appropriate amine.

The new compounds of the formulae (I) and (Ia) possess valuable pharmaceutical properties. These compounds exert, among others, antiphlogistic, analgesic, narcosis potentiating and tetrabenazine antagonizing effects.

The toxicity of the new compounds according to the invention was determined on mice after oral administration. The $LD_{50}$ values observed are listed in Table 1. The chemical names of the reference compounds are as follows:

Meprobamate: 2-methyl-2-propyl-1,3-propanediol dicarbamate;
Paracetamol: N-(hydroxyphenyl)acetamide;
Phenylbutazone: 4-butyl-1,2-diphenyl-3,5-pyrazolidinedione.

TABLE 1

| Compound No. of Example | $LD_{50}$ mg/kg |
|---|---|
| 1 | 1100 |
| 3 | 2000 |

TABLE 1-continued

| Compound No. of Example | LD$_{50}$ mg/kg |
| --- | --- |
| 4 | 1750 |
| 5 | 1000 |
| 11 | 2000 |
| Meprobamate | 1100 |
| Paracetamol | 510 |
| Phenylbutazone | 1000 |
| Acetylsalicylic acid | 1500 |

The analgesic effect of the new compounds according to the invention was determined on mice by the acetic acid writhing test. The animals were treated orally with the active agent; those belonging to the control group received vehicle only. One hour after this treatment 0.4 ml of a 0.5% acetic acid solution were administered into the animals, and the number of writhings observed within a period of 5 minutes was registered. The results observed on the treated groups were expressed as percents in relation to the controls. The ED$_{50}$ values and the therapeutical indices are listed in Table 2.

TABLE 2

| Compound No. of Example | ED$_{50}$ mg/kg | Therapeutical index |
| --- | --- | --- |
| 3 | 200 | 10 |
| 4 | 175 | 10 |
| 5 | 100 | 10 |
| Paracetamol | 180 | 2.8 |

The antiphlogistic (oedema-inhibiting) effect was tested on rats. 0.1 ml of a 1% carrageenin solution were injected into the plantar region of one of the hind paws. The volume of the paw was measured just before and 3 hours after the introduction of the oedema-provoking agent by a mercury plethysmometer. The dosages which inhibit the inflammation by 30% (ED$_{30}$; significant effect) are listed in Table 3.

TABLE 3

| Compound No. of Example | ED$_{30}$ mg/kg | Therapeutical index |
| --- | --- | --- |
| 1 | 110 | 10 |
| 4 | 22 | 79.55 |
| Phenylbutazone | 90 | 11.1 |
| Acetylsalicylic acid | 180 | 8.33 |

The narcosis potentiating effect was determined on mice by the method of Kaergaard (Arch. Int. Pharmacodyn. 2, 170/1967/). The results are listed in Table 4.

TABLE 4

| Compound No. of Example | ED$_{50}$ mg/kg | Therapeutical index |
| --- | --- | --- |
| 1 | 75 | 15 |
| 3 | 80 | 25 |
| 4 | 140 | 13 |
| 5 | 140 | 7 |
| Meprobamate | 260 | 4.2 |

The invention also relates to pharmaceutical compositions containing at least one compound of the formula (I) or (Ia) or a pharmaceutically acceptable acid addition salt thereof. These pharmaceutical compositions contain conventional solid or liquid pharmaceutical carriers (such as magnesium carbonate, magnesium stearate, starch, calcium carbonate, talc, water, vaseline, polyethylene glycol, etc.). The pharmaceutical compositions may also contain appropriate pharmaceutical auxiliary agents and/or additional pharmaceutically active components. The pharmaceutical compositions can be prepared in solid (e.g. tablets, coated tablets, capsules, etc.) or liquid (e.g. solutions, suspensions, emulsions, etc.) form. The pharmaceutical compositions are prepared by methods generally known in the pharmaceutical industry.

The new compounds according to the invention can be applied in the therapy preferably in daily oral dosages of about 50 to 800 mg. These values are given, however, only for information, since the actual dosages always depend on the given conditions (e.g. state and general health of the patient, activity of the compound, prescription of the physician, etc.), thus they may also be lower or higher than the limits given above.

The invention is elucidated in detail by the aid of the following non-limiting Examples.

EXAMPLE 1

Preparation of 4,5-diacetyl-4,5-dihydro-s-triazolo-[3,4-c]benzo-as-triazine 7.0 g (0.04 mole) of 4,5-dihydro-s-triazolo[3,4-c]-benzo-as-triazine are added to a mixture of 35 ml of glacial acetic acid and 35 ml of acetic anhydride, and the reaction mixture is refluxed for 6 hours. At the end of the reaction the mixture is cooled, the product is precipitated with ether and filtered off. 9.4 g of the title compound are obtained; yield: 91%; m.p.: 186°–188° C.

Analysis: calculated N%=27.20, found N%=26.95.
Mol.wt.: 257 (on the basis of mass spectrum).

EXAMPLE 2

Preparation of 1-(N-methyl-piperazino)-4,5-dipropionyl-4,5-dihydro-s-triazolo[3,4-c]benzo-as-triazine A mixture of 12.0 g (0.048 mole) of 1-bromo-s-triazolo[3,4-c]benzo-as-triazine, 40 ml of N-methyl-piperazine and 80 ml of ethanol is refluxed for 2 hours. The solution is poured into water and the product is extracted mit methylene chloride. The solvent is evaporated from the extract and the residue is recrystallized from benzene. 9.7 g (70%) of 1-(N-methyl-piperazino)-s-triazolo[3,4-c]benzo-as-triazine are obtained; m.p.: 162°–163° C. This product is added to a suspension of 12 g (0.068 moles) of sodium dithionite in 100 ml of water, and reduced into the respective dihydro compound under argon atmosphere. The separated precipitate is filtered off, dried, admixed with 50 ml of propionic anhydride, and the mixture is heated at 120° to 125° C. for 2 hours. The reaction mixture is cooled and the separated product is filtered off. 12.3 g (67.0%) of the title compound are obtained; m.p.: 173°–175° C.

Analysis: calculated N%=21.90, found N%=21.75.
Mol.wt.: 382 (on the basis of mass spectrum).

EXAMPLE 3

Preparation of 4,5-dipropionyl-4,5-dihydro-s-triazolo[3,4-c]benzo-as-triazine

A mixture of 4.0 g (0.023 mole) of 4,5-dihydro-s-triazolo[3,4-c]benzo-as-triazine and 50 ml of propionic anhydride is heated at 120° to 125° C. for one hour. The reaction mixture is cooled and the product is precipitated with ether. 3.5 g (53.4%) of the title compound are obtained; m.p.: 192°–193° C.

Analysis: calculated N% = 30.50; found N% = 30.15.
Mol.wt.: 229 (on the basis of mass spectrum)

EXAMPLE 4

Preparation of 5-propionyl-4,5-dihydro-s-triazolo[3,4-c]benzo-as-triazine 5.0 g (0.017 mole) of 4,5-dipropionyl-4,5-dihydro-s-triazolo[3,4-c]benzo-as-triazine are treated with 50 ml of a 5% sodium hydroxide solution. The solution which forms within a short time is decolourized, filtered, the filtrate is acidified with acetic acid, and the separated colourless precipitate is filtered off. 2.5 g (63%) of the title compound are obtained; m.p.: 244° C.

Analysis: calculated N% = 30.60; found N% = 30.45.
Mol.wt.: 229 (on the basis of mass spectrum)

EXAMPLE 5

Preparation of 1-methylthio-4,5-dipropionyl-4,5-dihydro-s-triazolo[3,4-c]benzo-as-triazine 10.0 g (0.046 mole) of 1-methylthio-s-triazolo[3,4-c]benzo-as-triazine and 12 g (0.068 mole) of sodium dithionite are suspended in 100 ml of water, and 20 ml of ethanol are added to the suspension. A solution is formed, and a precipitate starts to separate from it within a short time. After 30 minutes the precipitate is separated by filtration from the cold mixture. The resulting 1-methylthio-4,5-dihydro-s-triazolo[3,4-c]benzo-as-triazine (7.2 g, 71%) is reacted with 65 ml of propionic anhydride at 120° C. for 2 hours under argon atmosphere. The reaction mixture is evaporated and the residue is crystallized from a mixture of methylene chloride and petroleum ether. 8.0 g (80%) of the title compound are obtained; m.p.: 119°–120° C.

Analysis: calculated N% = 21.13; found N% = 21.02.
Mol.wt.: 331 (on the basis of mass spectrum)

EXAMPLE 6

Preparation of 2,4,5-tripropionyl-4,5-dihydro-s-triazolo[3,4-c]benzo-as-triazine-1(2H)-one 12.0 g (0.064 mole) of s-triazolo[3,4-c]benzo-as-triazine-1(2H)-one are reduced with a solution of 16.0 g (0.092 moles) of sodium dithionite in 120 ml of water and 30 ml of ethanol. The resulting 4,5-dihydro-s-triazolo[3,4-c]benzo-as-triazine-1(2H)-one, obtained with a yield of 80%, is acylated with 80 ml of propionic anhydride as described in Example 5. 12.0 g (65%) of the title compound are obtained; m.p.: 205°–206° C.

Analysis: calculated N% = 19.59; found N% = 19.39.
Mol.wt.: 357 (on the basis of mass spectrum)

EXAMPLE 7

Preparation of 7-chloro-2,4,5-tripropionyl-4,5-dihydro-s-triazolo[3,4-c]benzo-as-triazine-1(2H)-one 4,5-Dihydro-7-chloro-s-triazolo[3,4-c]benzo-as-triazine-1(2H)-one, obtained with a yield of 72% from 10.0 g (0.045 mole) of 7-chloro-s-triazolo[3,4-c]benzo-as-triazine-1(2H)-one, is acylated with propionic anhydride as described in Example 5. 8.9 g (51%) of the title compound are obtained; m.p.: 193°–194° C.

Analysis: calculated N% = 17.88; found N% = 17.83.
Mol.wt.: 391 (on the basis of mass spectrum)

EXAMPLE 8

Preparation of 5-acetyl-4,5-dihydro-s-triazolo[3,4-c]benzo-as-triazine

The title compound is prepared from 5.0 g (0.019 mole) of 4,5-diacetyl-4,5-dihydro-s-triazolo[3,4-c]benzo-as-triazine according to the method of Example 4. Yield: 1.71 g(42%); m.p.: 219°–220° C.

Analysis: calculated N% = 32.54; found N% = 32.36.
Mol.wt.: 215 (on the basis of mass spectrum)

EXAMPLE 9

Preparation of 4,5-dicinnamoyl-4,5-dihydro-s-triazolo[3,4-c]benzo-as-triazine

A mixture of 4.0 g (0.023 mole) of 4,5-dihydro-s-triazolo[3,4-c]benzo-as-triazine, 7.66 g (0.046 mole) of cinnamoyl chloride and 70 ml of dimethyl formamide is refluxed for 4 hours, and the mixture is processed in the usual way. 7.48 g (75%) of the title compound are obtained; m.p.: 220°–221° C.

Analysis: calculated N% = 16.16; found N% = 16.02.
Mol.wt.: 433 (on the basis of mass spectrum)

EXAMPLE 10

Preparation of 1-oxo-3-hydroxy-2-n-butyl-pyrazolo[1,2-a]-s-triazolo[3,4-c]benzo-as-triazine 3.6 ml (0.023 mole) of n-butyl-malic acid dichloride are added to a suspension of 4.0 g (0.023 mole) of 4,5-dihydro-s-triazolo[3,4-c]benzo-as-triazine in 80 ml of dioxane, and the mixture is allowed to stand at 60° C. for 2 hours. 3.7 g (54%) of the title compound are obtained; m.p.: 300° C.

Analysis: calculated N% = 23.50; found N% = 23.15.
Mol.wt.: 297 (on the basis of mass spectrum)

EXAMPLE 11

Preparation of 1-oxo-3-hydroxy-2-n-propyl-pyrazolo[1,2-a]-s-triazolo[3,4-c]benzo-as-triazine 4,5-Dihydro-s-triazolo[3,4-c]benzo-as-triazine is reacted with n-propyl-malonic acid dichloride as described in Example 10. 3.45 g (53%) of the title compound are obtained; m.p.: 301° C.

Analysis: calculated N% = 24.70; found N% = 24.45.
Mol.wt.: 283 (on the basis of mass spectrum)

EXAMPLE 12

Preparation of 4,5-diacetyl-4,5-dihydro-s-triazolo[3,4-c]benzo-as-triazine

A mixture of 5 g (0.028 mole) of 4,5-dihydro-s-triazolo[3,4-c]benzo-as-triazine, 4.8 g (0.062 mole) of acetyl chloride and 50 ml of dimethyl formamide is heated at 60° C. for 0.5 hours under argon atmosphere. The reaction mixture is cooled and poured onto ice. The product is extracted into methylene chloride, and the solvent is evaporated. 6.0 g (72%) of the title compound are obtained; m.p.: 186° C.

Analysis: calculated N% = 27.20; found N% = 27.10.
Mol.wt.: 257 (on the basis of mass spectrum)

EXAMPLE 13

Preparation of 4,5-bis-phenylacetyl-4,5-dihydro-s-triazolo[3,4-c]benzo-as-triazine 5 g (0.028 mole) of 4,5-dihydro-s-triazolo[3,4-c]benzo-as-triazine are reacted with 9.8 g (0.064 mole) of phenylacetyl chloride as described in Example 12. 7.33 g (64%) of the title compound are obtained; m.p.: 150°–151° C.

Analysis: calculated N% = 17.11; found N% = 17.20.
Mol.wt.: 409 (on the basis of mass spectrum)

EXAMPLE 14

Preparation of 4,5-dibenzoyl-4,5-dihydro-s-triazolo[3,4-c]benzo-as-triazine

One proceeds as described in Example 12 with the difference that benzoyl chloride is applied as acylating agent instead of acetyl chloride. 5.33 g (50%) of the title compound are obtained; m.p.: 225°–226° C.

Analysis: calculated N% = 18.37; found N% = 18.12.
Mol.wt.: 381 (on the basis of mass spectrum)

EXAMPLE 15

Preparation of 4,5-bis(chloroacetyl)-4,5-dihydro-s-triazolo[3,4-c]benzo-as-triazine One proceeds as described in Example 12 with the difference that chloroacetyl chloride is applied as acylating agent instead of acetyl chloride. 6.2 g (68%) of the title compound are obtained; m.p.: 300° C.

Analysis: calculated N% = 21.47; found N% = 21.32.
Mol.wt.: 326 (on the basis of mass spectrum)

EXAMPLE 16

Preparation of 4,5-dinicotinoyl-4,5-dihydro-s-triazolo[3,4-c]benzo-as-triazine dihydrochloride One proceeds as described in Example 12 with the difference that nicotinoyl chloride is applied as acylating agent instead of acetyl chloride. The resulting 4,5-dinicotinoyl-4,5-dihydro-s-triazolo[3,4-c]benzo-as-triazine, obtained with a yield of 71%, is treated with alcoholic hydrochloric acid to obtain the respective dihydrochloride; m.p.: 227°–228° C.

Analysis: calculated N% = 19.00; found N% = 18.89.
Mol.wt.: 442 (on the basis of mass spectrum)

EXAMPLE 17

Preparation of 4,5-distearoyl-4,5-dihydro-s-triazolo[3,4-c]benzo-as-triazine

A mixture of 5 g (0.029 mole) of 4,5-dihydro-s-triazolo[3,4-c]benzo-as-triazine, 2 g (0.066 mole) of stearoyl chloride and 50 ml of dry dimethyl formamide is heated at 60° C. for one hour under argon atmosphere. The reaction mixture is poured onto ice and the product is filtered off. 8 g (45%) of the title compound are obtained; m.p.: 77°–78° C.

Analysis: calculated N% = 11.62; found N% = 11.52.
Mol.wt.: 606 (on the basis of mass spectrum)

EXAMPLE 18

Preparation of 1-morpholino-4,5-dipropionyl-4,5-dihydro-s-triazolo[3,4-c]benzo-as-triazine A mixture of 4 g (0.0014 mole) of 1-morpholino-4,5-dihydro-s-triazolo[3,4-c]benzo-as-triazine and 40 ml of propionic anhydride is heated at 80° C. for one hour under argon atmosphere. The reaction mixture is evaporated and the residue is treated with ether. The product separates in crystalline form. 3.9 g (69%) of the title compound are obtained; m.p.: 128°–129° C.

Analysis: calculated N% = 22.68; found N% = 22.58.
Mol.wt.: 270 (on the basis of mass spectrum)

EXAMPLE 19

Preparation of 1-(N-methyl-piperazino)-4,5-diethoxycarbonyl-4,5-dihydro-s-triazolo[3,4-c]benzo-as-triazine The title compound is obtained with a yield of 85% when reacting 1-(N-methyl-piperazino)-4,5-dihydro-s-triazolo[3,4-c]benzo-as-triazine with ethyl chloroformate as described in Example 10. M.p.: 212°–213° C.

Analysis: calculated N% = 23.60; found N% = 23.45.
Mol.wt.: 415 (on the basis of mass spectrum)

EXAMPLE 20

Preparation of 7-methyl-4,5-dipropionyl-4,5-dihydro-s-triazolo[3,4-c]benzo-as-triazine The title compound is obtained with a yield of 78% when reacting 7-methyl-4,5-dihydro-s-triazolo[3,4-c]benzo-as-triazine with propionic anhydride as described in Example 18. M.p.: 226°–228° C.

Analysis: calculated N% = 24.40; found N% = 24.15.
Mol.wt.: 287 (on the basis of mass spectrum)

EXAMPLE 21

Preparation of 5-propionyl-4,5-dihydro-s-triazolo[3,4-c]benzo-as-triazine

A mixture of 4.0 g (0.023 mole) of 4,5-dihydro-s-triazolo[3,4-c]benzo-as-triazine, 2.2 g (0.023 mole) of propionyl chloride and 50 ml of benzene is refluxed under nitrogen atmosphere. The reaction mixture is cooled and the separated product is filtered off. The title compound, melting at 244° C., is obtained with a yield of 70%. The product does not show melting point depression in admixture with the compound prepared according to Example 4.

EXAMPLE 22

Preparation of 5-acetyl-4,5-dihydro-s-triazolo[3,4-c]benzo-as-triazine

A mixture of 7.0 g (0.040 mole) of 4,5-dihydro-s-triazolo[3,4-c]benzo-as-triazine, 3.1 g (0.04 mole) of acetyl chloride and 50 ml of toluene is refluxed under nitrogen atmosphere. The reaction mixture is cooled. The title compound, melting at 220° C., is obtained with a yield of 70%. The product does not show melting point depression in admixture with the compound prepared according to Example 8.

What we claim is:

1. A benzo-as-triazine derivative of the formula (I) or (Ia) or a pharmaceutically acceptable acid addition salt thereof,

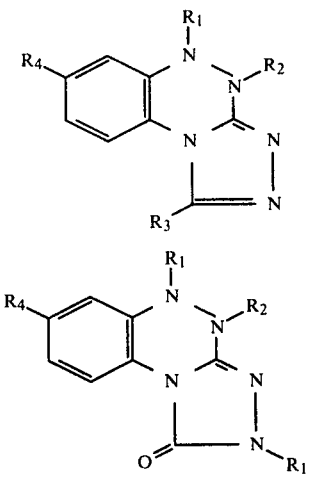

(I)

(Ia)

wherein

R₁ and R₂ each represent hydrogen, a $C_{1-20}$ alkylcarbonyl group, a phenylcarbonyl or phenyl-($C_{1-4}$ alkyl)-carbonyl group having optionally one or more halogen, hydroxy or $C_{1-3}$ alkoxy substituents which may be the same or different, furthermore a pyridylcarbonyl, a pyrazinylcarbonyl, a furylcarbonyl, a chloroacetyl or a $C_{1-4}$ alkoxycarbonyl group, or R₁ and R₂ may form, together with the adjacent nitrogen atoms, a pyrazole ring having optionally a $C_{1-6}$ alkyl substituent in position 4, with the proviso that one of R₁ and R₂ is always different from hydrogen, R₃ stands for hydrogen, mercapto group, a $C_{1-4}$ alkylmercapto group, amino group, a $C_{1-4}$ alkylamino group, a piperazino group having optionally an N-alkyl or 2-pyridyl substituent, a morpholino group or a piperidino group, and R₄ stands for hydrogen, halogen, $C_{1-4}$ alkyl or $C_{1-4}$ alkoxy group.

2. A compound as claimed in claim 1, wherein R₁ and R₂ each represent hydrogen, acetyl, propionyl, stearoyl, benzoyl, phenylacetyl, chloroacetyl, or nicotinoyl, or R₁ and R₂ form together with the adjacent nitrogen atoms a 1,3-dioxo-2-n-butyl-pyrazole or 1,3-dioxo-2-n-propyl-pyrazole group, with the proviso that at least one of R₁ and R₂ is other than hydrogen, or a pharmaceutically acceptable acid addition salt thereof.

3. A compound as claimed in claim 1, selected from the group consisting of 4,5-diacetyl-4,5-dihydro-s-triazolo[3,4-c]benzo-as-triazine, 4,5-dipropionyl-4,5-dihydro-s-triazolo[3,4-c]benzo-as-triazine, 5-propionyl-4,5-dihydro-s-triazolo[3,4-c]benzo-as-triazine, 1-methylthio-4,5-dipropionyl-4,5-dihydro-s-triazolo[3,4-c]benzo-as-triazine, 2,4,5-tripropionyl-4,5-dihydro-s-triazolo[3,4-c]benzo-as-triazine-1(2H)-one, 2-n-butyl-1-oxo-3-hydroxy-pyrazolo[1,2-a]-s-triazolo[3,4-c]benzo-as-triazine, 2-n-propyl-1-oxo-3-hydroxy-pyrazolo[1,2-a]-s-triazolo[3,4-c]benzo-as-triazine, or a pharmaceutically acceptable acid addition salt, particularly hydrochloride, thereof.

* * * * *